United States Patent
Matsui

(10) Patent No.: US 8,493,557 B2
(45) Date of Patent: Jul. 23, 2013

(54) SURFACE INSPECTING APPARATUS AND SURFACE INSPECTING METHOD

(75) Inventor: Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 48 days.

(21) Appl. No.: 13/202,681

(22) PCT Filed: Jan. 22, 2010

(86) PCT No.: PCT/JP2010/050851
§ 371 (c)(1),
(2), (4) Date: Nov. 2, 2011

(87) PCT Pub. No.: WO2010/100973
PCT Pub. Date: Sep. 10, 2010

(65) Prior Publication Data
US 2012/0044505 A1    Feb. 23, 2012

(30) Foreign Application Priority Data

Mar. 6, 2009  (JP) .................. 2009-053921

(51) Int. Cl.
*G01N 21/00* (2006.01)

(52) U.S. Cl.
USPC ....................... 356/237.1; 356/426

(58) Field of Classification Search
USPC .................. 356/237.1–237.6, 426–428
See application file for complete search history.

(56) References Cited

U.S. PATENT DOCUMENTS

| | | | |
|---|---|---|---|
| 6,529,270 | B1 | 3/2003 | Bills |
| 2006/0256325 | A1 | 11/2006 | Mcmillan et al. |
| 2007/0268484 | A1 | 11/2007 | Matsui |
| 2008/0027665 | A1* | 1/2008 | Takahashi et al. .............. 702/70 |

FOREIGN PATENT DOCUMENTS

| | | |
|---|---|---|
| JP | 53-028772 U | 3/1978 |
| JP | 61-133843 | 6/1986 |
| JP | 63-033651 | 2/1988 |
| JP | 2000-329709 | 11/2000 |
| JP | 2007-309713 | 11/2007 |
| JP | 2008-008803 | 1/2008 |
| JP | 2008-020359 | 1/2008 |
| JP | 2008-032582 | 2/2008 |

OTHER PUBLICATIONS

Japanese Office Action, and English translation thereof, issued in Japanese Patent Application No. 2009-053921 dated Jul. 31, 2012.

* cited by examiner

Primary Examiner — Tara S Pajoohi Gomez
(74) Attorney, Agent, or Firm — McDermott Will & Emery LLP

(57) ABSTRACT

A surface inspecting apparatus rotates a semiconductor wafer 100 (inspection object) as a main scan while translating the semiconductor wafer 100 as an auxiliary scan, illuminates the surface of the semiconductor wafer 100 with illuminating light 21, thereby forms an illumination spot 3 as the illumination area of the illuminating light 21, detects scattered or diffracted or reflected light from the illumination spot, and detects a foreign object existing on the surface of the semiconductor wafer 100 or in a part of the semiconductor wafer 100 in the vicinity of the surface based on the result of the detection. In the surface inspecting apparatus, the translation speed of the auxiliary scan is controlled according to the distance from the rotation center of the semiconductor wafer 100 in the main scan to the illumination spot. With this control, the inspection time can be shortened while the deterioration in the detection sensitivity and the increase in the thermal damage during the surface inspection are suppressed.

10 Claims, 4 Drawing Sheets

SURFACE INSPECTING APPARATUS AND SURFACE INSPECTING METHOD

RELATED APPLICATIONS

This application is the U.S. National Phase under 35 U.S.C. §371 of International Application No. PCT/JP2010/050851, filed on Jan. 22, 2010, which in turn claims the benefit of Japanese Application No. 2009-053921, filed on Mar. 6, 2009, the disclosures of which Applications are incorporated by reference herein.

TECHNICAL FIELD

The present invention relates to an inspecting apparatus and an inspecting method for detecting a foreign substance, flaw, defect, dirt, etc. (hereinafter collectively referred to as a "foreign object") existing on the surface of a semiconductor substrate, thin film substrate, etc.

BACKGROUND ART

It is important to suppress deterioration in product quality and manufacturing yield in the manufacturing process of a semiconductor substrate, thin film substrate, etc. (hereinafter collectively referred to as an "inspection object"). During such a manufacturing process, dust generation around the manufacturing equipment and cleanness of the manufacturing process are monitored by detecting and managing foreign substances, flaws, defects, dirt, etc. (hereinafter collectively referred to as "foreign objects") on the surface of the inspection object.

Examples of an apparatus for detecting foreign objects on the surface of an inspection object include surface inspection apparatuses as described in Patent Literatures 1 and 2. Such a surface inspection apparatus illuminates the surface of the inspection object with inspection light at a fixed position, and moves (translates) the illuminated inspection object in a direction while the object is rotated. With this operation, the surface of the inspection object is spirally scanned with the area illuminated with the inspection light (hereinafter referred to as an "illumination spot"). By detecting scattered light generated at the surface of the substrate to be inspected surface, the inspection apparatus detects a foreign object existing on the surface of the inspection object or in a part of the inspection object in the vicinity of the surface. It is to be noted that a "main scan" means a scan in the direction of the rotation of the inspection object while an "auxiliary scan" means a scan in a direction orthogonal to the main scan.

An apparatus disclosed in Patent Literature 3 is designed to be capable of changing the diameter of the illumination spot (measured in the main scan direction) on the inspection object. The illumination spot's diameter in the main scan direction is changed such that the diameter increases as the illumination spot approaches the rotation center of the inspection object (decreases as the illumination spot moves away from the rotation center). By the control of the illumination spot's diameter, the surface temperature rise of the inspection object and the detection sensitivity to foreign substances/defects are maintained substantially constant during the inspection. Meanwhile, Patent Literatures 4 and 5 have disclosed a technique in which multiple illumination spots with fixed diameters are formed on the surface of the inspection object and scattered light from the illumination spots is detected.

PRIOR ART LITERATURE

Patent Literature

Patent Literature 1: JP-2007-309713-A
Patent Literature 2: JP-2008-32582-A
Patent Literature 3: US Patent Publication No. 2006/0256325
Patent Literature 4: JP-2008-8803-A
Patent Literature 5: JP-2008-20359-A

SUMMARY OF THE INVENTION

Problem to be Solved by the Invention

For the surface inspection of semiconductor substrates, thin film substrates, etc. (inspection objects), the foreign object required for detection rapidly decreases in size and the area to be inspected for the inspection object tends to increase in recent years. As a result, an increase in the time it takes to inspect an inspection object is becoming a concern these days.

One of methods conceivable for shortening the time it takes for the surface inspection is to increase the revolving speed of the inspection object. However, an inspecting apparatus based on such a method is in most cases operated at the upper limit revolving speed set in consideration of the strength of the inspection object and the strength with which to fix the inspection object to the apparatus. Thus a further increase in the revolving speed cannot be expected.

Further, conceivable another method for shortening the inspection time is as follows. The area to be scanned with the illumination spot during one rotation of the inspection object is enlarged by increasing the diameter of the illumination spot in the auxiliary scan direction (with the illuminance of the illumination spot kept at a constant level) and correspondingly increasing the feeding pitch (translation speed) in the auxiliary scan direction.

However, the increasing of the illumination spot's diameter in the auxiliary scan direction with the illumination spot's illuminance kept at a constant level leads to an increase of background scattered light (caused by minute roughness of the surface of the inspection object), resulting in a deterioration in the detection sensitivity to the foreign object. In contrast, if the illuminance of the illumination spot is increased, the deterioration in the detection sensitivity can be somewhat suppressed; however this leads to an increase in thermal damage to the inspection object.

The present invention has been made in consideration of the situation described above, and the object of the present invention is to provide a surface inspecting apparatus and a surface inspecting method capable of shortening the inspection time while the deterioration in the detection sensitivity and the increase in the thermal damage during the surface inspection are suppressed.

Means for Solving the Problem

In accordance with an aspect of the present invention, there is provided a surface inspecting method employing a surface inspecting apparatus, the surface inspecting apparatus comprising inspection object moving means for rotating an inspection object as a main scan and translating the inspection object as an auxiliary scan, illuminating means for illuminating a surface of the inspection object with illuminating light and thereby forming an illumination spot as an illumination area of the illuminating light, optical detector means for detecting scattered/diffracted/reflected light from the illumination spot, and foreign object detecting means for detecting a foreign object existing on the surface of the inspection object or in a part of the inspection object in the vicinity of the surface based on a result of the detection supplied from the optical detector means. Translation speed of the auxiliary scan by the inspection object moving means is controlled according to distance from a rotation center of the inspection object in the main scan to the illumination spot.

Effect of the Invention

According to the present invention, the inspection time can be shortened while the deterioration in the detection sensitivity and the increase in the thermal damage during the surface inspection are suppressed.

MODE FOR CARRYING OUT THE INVENTION

Figure 1:
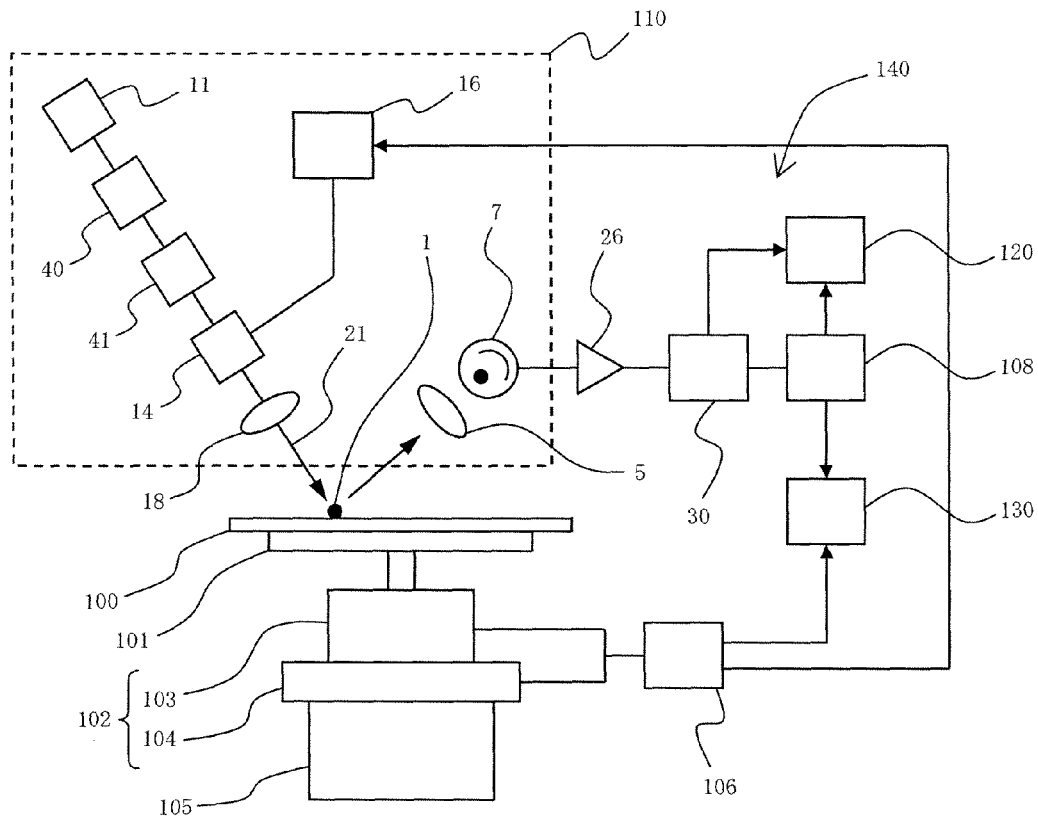
FIG. 1 is a schematic block diagram showing the overall configuration of a surface inspecting apparatus in accordance with a first embodiment of the present invention.

Referring now to the drawings, a description will be given in detail of preferred embodiments in accordance with the present invention.

First Embodiment

FIG. 1 is a schematic block diagram showing the overall configuration of a surface inspecting apparatus in accordance with a first embodiment of the present invention.

In FIG. 1, the surface inspecting apparatus of this embodiment includes a chuck 101, an inspection object moving stage 102, a Z stage 105, an illumination/detection optical system 110, and an illumination/detection control system 140. The chuck 101 holds a semiconductor wafer 100 (example of the inspection object) by vacuum suction. The inspection object moving stage 102 includes a rotating stage 103 for rotating the chuck 101 together with the semiconductor wafer 100 and a translating stage 104 for translating (moving in a direction) the chuck 101 together with the semiconductor wafer 100.

The Z stage 105 moves the semiconductor wafer 100 in the vertical direction by moving the inspection object moving stage 102 and the chuck 101 in the vertical direction. The illumination/detection optical system 110, arranged over the semiconductor wafer 100, illuminates the surface of the semiconductor wafer 100 with illuminating light 21 and detects scattered/diffracted/reflected light from the surface of the semiconductor wafer 100. The illumination/detection control system 140 controls the illumination/detection operation of the inspection object moving stage 102 and the illumination/detection optical system 110.

The surface of the semiconductor wafer 100 is scanned with the illuminating light 21 by translating and rotating the semiconductor wafer 100 with the inspection object moving stage 102 while the wafer surface is illuminated with the illuminating light 21. Incidentally, a scan that is executed by the rotation of the semiconductor wafer 100 by the rotating stage 103 (i.e., a scan in the direction of the rotation) will be referred to as a "main scan", while a scan that is executed by the translation of the semiconductor wafer 100 by the translating stage 104 (i.e., a scan in a direction orthogonal to the main scan) will be referred to as an "auxiliary scan".

The illumination/detection optical system 110 includes a light source 11, a light amount adjustment mechanism 40, a beam expander 41, a beam width shaping optical system 14, a beam width control mechanism 16 and a lens 18. The light source 11 generates and emits laser light. The light amount adjustment mechanism 40 adjusts the optical intensity of the laser light emitted by the light source 11 by attenuating the laser light. The beam expander 41 adjusts the beam diameter of the laser light from the light amount adjustment mechanism 40. The beam width shaping optical system 14 shapes the laser light from the beam expander 41 into a parallel beam (parallel pencil of light) having a prescribed beam diameter. The beam width control mechanism 16 controls the operation of the beam width shaping optical system 14. The lens 18 is used for illuminating the surface of the semiconductor wafer 100 with the laser light from the beam width shaping optical system 14 as the illuminating light 21 and thereby forming an illumination spot 3 (see FIG. 7 which will be explained later).

The beam width shaping optical system 14 has the function of shaping the sectional shape of the illuminating light 21 into an elliptical shape by compressing the sectional shape in a prescribed direction. The beam width control mechanism 16 controls the beam width shaping optical system 14 and thereby changes the aspect ratio of the sectional shape of the elliptically shaped illuminating light 21 between 1:1 and 1:1/8. Incidentally, the intensity of the whole illuminating light 21 is kept constant irrespective of the sectional shape (aspect ratio) of the illuminating light 21.

The surface inspecting apparatus is configured so that the illuminating light 21 (P-polarized light, for example) is obliquely incident upon the surface of the semiconductor wafer 100 substantially at the Brewster's angle with respect to the crystalline Si. Therefore, the illumination spot 3 is formed in a substantially elliptical shape, with its major axis oriented in the auxiliary scan direction of the inspection object moving stage 102, that is, in a direction orthogonal to the main scan direction.

Here, the illumination spot 3 is defined anew as a region inside a border line where the illuminance drops to $1/e^2$ (e: the base of natural logarithm) of that at the center of the illumination spot 3. The widths of the illumination spot 3 in the major axis direction and in the minor axis direction are assumed to be d1 and d2, respectively. In the beam width shaping optical system 14, the direction of the compression of the laser light's sectional shape corresponds to the direction of the major diameter d1, while the minor diameter d2 is kept constant. When the compression rate of the aspect ratio in the beam width shaping optical system 14 equals 1:1/K (1≦K≦8), the relationship between d1 and d2 is represented by the following equation:

$$d_1 = \frac{K \times d_2}{\cos\theta} \quad \text{(Equation 1)}$$

The illumination/detection optical system 110 further includes a condensing lens 5 and an optical detector 7. The condensing lens 5 is required to efficiently capture scattered light (scattered or diffracted or reflected light) from a microscopic foreign object 1 (foreign substance, flaw, defect, dirt, etc.) complying with (causing) Rayleigh scattering. Thus, the condensing lens 5 is arranged to be able to condense the scattered light at a low elevation angle. The optical detector 7 (e.g., photomultiplier tube) detects the scattered light from the foreign object 1. While a photomultiplier tube is used as the optical detector 7 in this embodiment, it is of course possible to employ a different optical detector based on a different principle of detection as long as the scattered light from the foreign object 1 can be detected with high sensitivity.

The illumination/detection control system 140 includes an amplifier 26, an A/D converter 30, a particle size calculating mechanism 120, a foreign substance/defect judgment mechanism 108, a foreign substance/defect coordinate detecting mechanism 130 and an inspection coordinate detecting mechanism 106.

A scattered light signal from the optical detector 7 is amplified by the amplifier 26 and then converted into digital data by the A/D converter 30 by sampling the signal at preset sampling intervals. The sampling interval of the A/D converter 30 has been set so that one rotation of the main scan is divided into equal (substantially fixed) angular intervals. The scattered light signal corresponding to the foreign object 1 is generated continuously throughout a time period during which the foreign object 1 crosses the width d2 of the illumination spot 3 in the minor axis direction. Therefore, a statistical calculation process covering the total number of sampling points corresponding to the time period is executed to the digital data. The averaged digital data after undergoing the statistical calculation process is compared with a preset detection threshold value by the foreign substance/defect judgment mechanism 108. If the averaged digital data is the threshold value or higher, the foreign substance/defect judgment mechanism 108 judges that the averaged digital data derives from a foreign substance/defect, monitors subsequent variations in the value of the averaged digital data, and generates foreign substance/defect judgment information upon detecting a maximum value. In response to the generation of the foreign substance/defect judgment information, the foreign substance/defect coordinate detecting mechanism 130 calculates the coordinate position of the detected foreign substance/defect. Subsequently, the particle size calculating mechanism 120 calculates the size of the detected foreign substance/defect from the maximum value of the averaged digital data. In this case, the magnitude of the averaged digital data caused by the foreign substance/defect changes proportionally to the illuminance of the illumination spot 3 even when the size of the foreign substance/defect is constant. Since the area of the illumination spot 3 is changed by the factor of K by the beam width shaping optical system 14, the averaged digital data to be used for the calculation of the size of the detected foreign substance/defect is previously corrected based on the change in the illuminance of the illumination spot 3 caused by the change in its area.

The inspection object moving stage 102 changes the rotation (angle) θ (main scan) and the translation (position) r (auxiliary scan) in combination and thereby makes the illumination spot 3 relatively and spirally scan substantially the entire surface of the semiconductor wafer 100. The inspection object moving stage 102 is provided with the inspection coordinate detecting mechanism 106 in order to detect a main scan coordinate position θ and an auxiliary scan coordinate position r in the inspection. While an optical scanning rotary encoder (not shown) and an optical scanning linear encoder are used in this embodiment for the detection of the main scan coordinate position θ and the auxiliary scan coordinate position r, respectively, it is of course possible to employ different sensors based on different principles of detection as long as the angle and the linear position can be detected with high sensitivity. While the scan with the illumination spot 3 is executed from the inner-radius part to the peripheral part of the semiconductor wafer 100, the scan may also be executed reversely.

Figure 2:
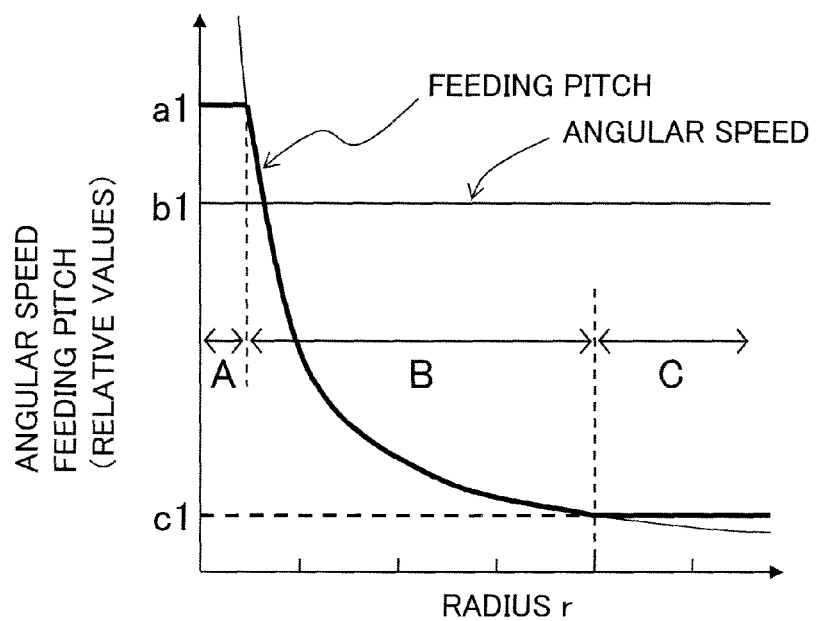
FIG. 2 is a graph showing an example of the relationship among the position, angular speed and feeding pitch of an illumination spot on the surface of an inspection object in the first embodiment of the present invention.

FIG. 2 is a graph showing an example of the relationship among the position, the angular speed and the feeding pitch of the illumination spot 3 on the surface of the inspection object in the first embodiment of the present invention.

In FIG. 2, the vertical axis represents the speed (angular speed) of the rotation of the semiconductor wafer 100 in the main scan direction by the rotating stage 103 of the inspection object moving stage 102 and the speed of the translation of the semiconductor wafer 100 in the auxiliary scan direction by the translating stage 104 (i.e., moving distance of the translating stage 104 in one rotation of the rotating stage (feeding pitch)). The horizontal axis represents the distance r from the center of the wafer 100 to the illumination spot 3 (hereinafter referred to as a "radius r"). The semiconductor wafer 100 is segmented into three areas A, B and C based on the radius r from the rotation center. The area A is the closest to the rotation center. The area C is the farthest from the rotation center (peripheral part of the semiconductor wafer 100). The area B is the intermediate area between the areas A and B.

The angular speed is constant (b1) irrespective of the radius r.

The feeding pitch is constant (a1) in the area A, decreases substantially inversely proportionally to the radius r in the area B, and is constant (c1) in the area C. Thus, the areas A, B and C will be referred to as an "inner constant feeding pitch area", a "feeding pitch control area" and an "outer constant feeding pitch area", respectively.

Incidentally, if the feeding pitch p is greater than $d_1$ (p>$d_1$), void areas not inspected (not illuminated with the illuminating light 21 in the helical scan with the illumination spot 3) are formed on the semiconductor wafer 100. Thus, in order to satisfy p≦$d_1$, the major diameter $d_1$ is also controlled substantially inversely proportionally to the radius r in sync with the aforementioned change in the feeding pitch p. This control is executed by the beam width control mechanism 16 by controlling the beam width shaping optical system 14. As a result of the above control of the main scan rotation angular speed, the auxiliary scan feeding pitch p and the major diameter $d_1$ of the illumination spot 3, an inspection areal speed as the product of the auxiliary scan feeding pitch p and the speed of the relative movement (linear speed) of the illumination spot 3 (at the radius r) in the main scan direction with respect to the surface of the semiconductor wafer 100 becomes substantially constant in the feeding pitch control area (area B) since the auxiliary scan feeding pitch p is inversely proportional to the radius r and the relative movement (linear) speed (angular speed×radius r) is proportional to the radius r. Further, since the averaged digital data is generated at the sampling intervals (dividing one main scan rotation into substantially equal angular intervals) as mentioned above, the number of pieces of averaged digital data per unit area on the surface of the semiconductor wafer 100 is substantially constant in the feeding pitch control area (area B).

In the surface inspecting apparatus configured as above, assuming that the radius of the semiconductor wafer 100 from the center to the periphery is R, the inspection time it takes for inspecting (scanning) the whole semiconductor wafer 100 is T, the total number of main scan rotations is M, the feeding pitch in the i-th rotation (included in the M rotations) is pi (mm), the main scan rotation speed is ωi (r/s), the time it takes for one rotation of the main scan is ΔTi (s), and the auxiliary scan speed is sufficiently slower than the main scan speed, the radius R and the inspection time T can be expressed by the following equations:

$$R = \sum_{i=1}^{M} P_i \quad \text{(Equation 2)}$$

$$T = \sum_{i=1}^{M} \Delta T_i = \sum_{i=1}^{M} \left(\frac{1}{\omega_i}\right) \quad \text{(Equation 3)}$$

Since the feeding pitch p is kept constant during the inspection as mentioned above, by letting pi=p0 (constant), the equation (2) is expressed as follows:

$$R = \sum_{i=1}^{M} P_i = Mp_0 \quad \text{(Equation 4)}$$

From the above equation (4), the total number M of main scan rotations necessary for inspecting (scanning) the whole semiconductor wafer 100 is expressed by the following equation:

$$M = \frac{R}{p_0} \quad \text{(Equation 5)}$$

By substituting the above equation (5) for M in the equation (3), the following relational expression is obtained:

$$T = \sum_{i=1}^{\frac{R}{p_0}} \left(\frac{1}{\omega_i}\right) \quad \text{(Equation 6)}$$

Since the main scan rotation mechanism of the inspection object moving stage 102 has an upper limit rotation speed ωmax, the above equation (5) is expressed as follows by use of ωmax:

$$T \geq \sum_{i=1}^{\frac{R}{p_0}} \left(\frac{1}{\omega_{max}}\right) = \frac{R}{p_0 \cdot \omega_{max}} \quad \text{(Equation 7)}$$

Thus, the following equation is obtained:

$$T_{min} = \frac{R}{p_0 \cdot \omega_{max}} \quad \text{(Equation 8)}$$

It is clear from the above equation (8) that in the case where the auxiliary scan feeding pitch is constant, the inspection time T cannot be shortened to less than Tmin even if the main scan rotation speed is kept at the upper limit rotation speed ωmax.

Next, the surface inspection time T (1), the detection sensitivity (2) and the thermal damage (3) will be examined by use of an example of numerical values.

(1) Surface Inspection Time T

First, a semiconductor wafer 100 with a diameter of 300 mm will be considered as an example. The inspection time it takes for inspecting (scanning) the whole area of the semiconductor wafer 100 is assumed to be T. The major diameter d1 of the illumination spot 3 and the feeding pitch pi in the i-th main scan rotation in each area (inner constant feeding pitch area (area A in FIG. 2), feeding pitch control area (area B in FIG. 2), outer constant feeding pitch area (area C in FIG. 2)) are defined as follows:

inner constant feeding pitch area: 0 mm≦r≦12.5 mm, d1=0.4 mm, pi=0.2 mm feeding pitch control area: 12.5 mm≦r≦100 mm, d1=5/r mm, pi=2.5/r mm outer constant feeding pitch area: 100 mm≦r≦150 mm, d1=0.05 mm, pi=0.025 mm The numbers of main scan rotations in each area defined as above are as follows:

inner constant feeding pitch area: 1≦i≦62 feeding pitch control area: 63≦i≦2030 outer constant feeding pitch area: 2031≦i≦4030

The total number M of main scan rotations is 4030 (M=4030).

If we assume here that d1=0.05 mm (constant) and pi=0.025 mm (constant) in all of the areas A, B and C, the total number M of main scan rotations amounts to 150/0.025=6000.

As above, in the case where the main scan rotation is executed at a constant angular speed, the surface inspection according to this embodiment is capable of reducing the inspection time to approximately (⅔)T in comparison with the inspection time T necessary when the inspection (scanning) is conducted by setting d1 and pi constant in all the areas of the semiconductor wafer 100.

(2) Detection Sensitivity

Next, the detection sensitivity to the foreign object will be examined. In this embodiment, the major diameter d1 of the illumination spot 3 and the auxiliary scan feeding pitch (translation speed) p are kept constant in the outer constant feeding pitch area (area C in FIG. 2). If these values are set equal to those in the conventional technique, the detection sensitivity naturally becomes equivalent to that in the conventional technique. Incidentally, since the illuminance of the illumination spot 3 is kept constant in this area, the detection sensitivity reaches the highest at the innermost part, that is, the boundary with the feeding pitch control area (area B in FIG. 2) where the linear speed is the slowest.

Next, the feeding pitch control area (area B in FIG. 2) will be considered. As mentioned above, the scattered light signal deriving from the foreign object 1 on the semiconductor wafer 100 may be presumed to be generated continuously throughout the time period during which the foreign object 1 crosses the minor diameter d2 of the illumination spot 3. In this case, a net signal quantity S of the scattered light signal obtained when the scattered light from the foreign object 1 is detected by the optical detector 7 is proportional to the <illuminance of the illumination spot> and inversely proportional to the <linear speed at the illumination spot position>. In this area, the <illuminance of the illumination spot> is controlled proportionally to the <radius r of the illumination spot position>. Since the <linear speed at the illumination spot position> is proportional to the <radius r of the illumination spot position> under the constant angular speed condition, the ratio between the two factors (<illuminance of the illumination spot>/<linear speed at the illumination spot position>) becomes constant. Meanwhile, the noise level N in the detection of the foreign object 1 is known to be proportional to the square root of the total illumination intensity per unit time, that is, the square root of <illuminance of the illumination spot>×<area of the illumination spot>. Since the intensity of the whole illuminating light 21 is kept constant in this embodiment irrespective of the changing of the <area of the illumination spot> as mentioned above, the effect on the noise level N is constant. Consequently, detection sensitivity substantially equal to that at the boundary with the outer constant feeding pitch area (area C in FIG. 2) can be achieved in this area.

Next, as for the inner constant feeding pitch area (area A in FIG. 2), the <illuminance of the illumination spot> is kept constant in this area similarly to the outer constant feeding pitch area (area C in FIG. 2). Therefore, the detection sensitivity is the lowest at the outermost part, that is, the boundary with the feeding pitch control area (area B in FIG. 2), and detection sensitivity in the whole area (inner constant feeding pitch area) is higher than that at the boundary. As explained above, it can be concluded in this embodiment that detection sensitivity equivalent to that in the conventional technique is achieved in the outer constant feeding pitch area (area C in FIG. 2) and at least detection sensitivity equivalent to or higher than that in the outer area can be secured in the areas inside the outer area.

(3) Thermal Damage

Next, the thermal damage to the semiconductor wafer 100 in the inspection will be examined. Since the intensity of the whole illuminating light 21 used for the illumination is kept substantially constant and the area of the illumination spot 3 increases with the decrease in the radius r in this embodiment as mentioned above, the illuminance of the illumination spot 3 decreases with the decrease in the radius r. It is well known that the thermal damage to the surface of the semiconductor wafer 100 in the inspection is substantially proportional to the illuminance of the illumination spot 3 when the relative linear speed of the illumination spot 3 (as the heat source) is constant. The linear speed in this embodiment is substantially equal to that in the conventional technique at each radius r and the illuminance of the illumination spot 3 in the inner parts is lower in this embodiment than in the conventional technique. Therefore, this embodiment is capable of reducing the thermal damage to the surface of the semiconductor wafer 100. Further, since the thermal damage decreases with the increase in the liner speed and the liner speed increases with the increase in the radius r of the position of the illumination spot 3, the thermal damage becomes light in the peripheral/outer part of the semiconductor wafer 100 (heavier with the decrease in the radius r) if the illuminance of the illumination spot 3 is constant. Since the illuminance of the illumination spot 3 in this embodiment decreases with the decrease in the radius r as mentioned above, this embodiment is capable of suppressing the increase in the thermal damage (which is light in the peripheral/outer part of the semiconductor wafer) with the decrease in the radius r.

In this embodiment configured as above, the auxiliary scan feeding pitch (translation speed) on the semiconductor wafer 100 is controlled according to the distance from the rotation center to the illumination spot 3 in the main scan of the semiconductor wafer 100. Therefore, the inspection time can be shortened while the deterioration in the detection sensitivity and the increase in the thermal damage during the surface inspection are suppressed.

Figure 3:
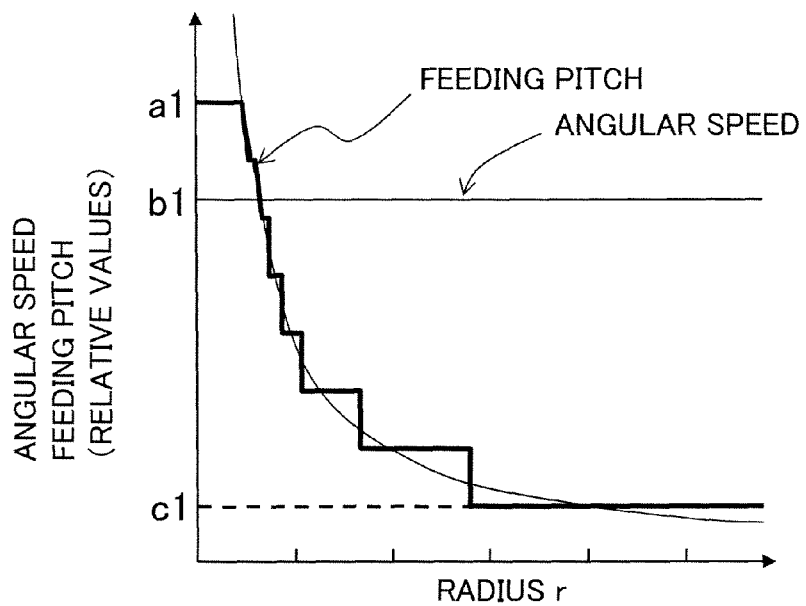
FIG. 3 is a graph showing another example of the relationship among the position, the angular speed and the feeding pitch of the illumination spot on the surface of the inspection object in the first embodiment of the present invention.

While the feeding pitch in this embodiment configured as above is decreased (controlled) substantially inversely proportionally to the radius r in the feeding pitch control area (area B in FIG. 2) as explained referring to FIG. 2, the control of the feeding pitch is not restricted to this example (it is satisfactory if the feeding pitch is controlled roughly inversely proportionally to the radius r). For example, effects similar to those of this embodiment can be achieved also when the feeding pitch is changed (decreased) stepwise roughly inversely proportionally to the radius r as shown in FIG. 3.

Second Embodiment

A second embodiment in accordance with the present invention will be described below referring to FIGS. 4 and 5.

Figure 4:
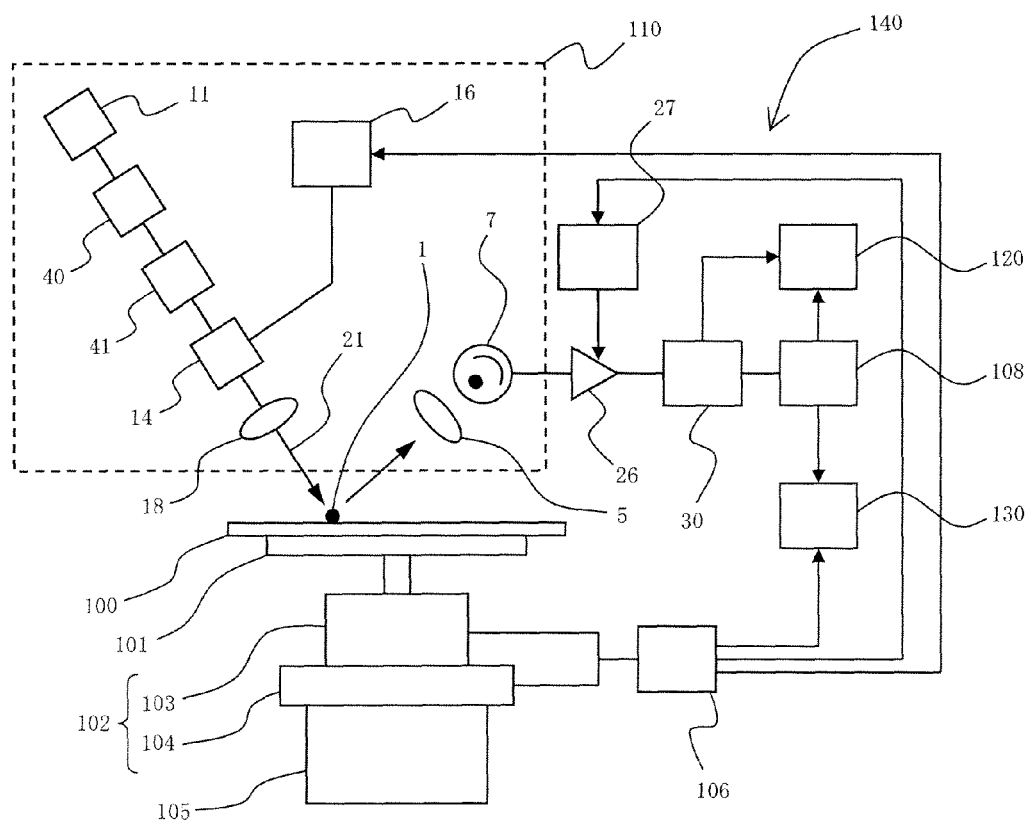
FIG. 4 is a schematic block diagram showing the overall configuration of a surface inspecting apparatus in accordance with a second embodiment of the present invention.

FIG. 4 is a schematic block diagram showing the overall configuration of a surface inspecting apparatus in accordance with the second embodiment of the present invention. FIG. 5 is a graph showing the relationship among the position, the angular speed and the feeding pitch of the illumination spot 3 on the surface of the inspection object in the second embodiment of the present invention. In FIGS. 4 and 5, elements equivalent to those shown in FIGS. 1 and 2 are assigned the same reference characters as those in the figures and repeated explanation thereof is omitted for brevity.

In FIG. 4, the surface inspecting apparatus of this embodiment includes a frequency bandwidth control unit 27 for controlling the frequency bandwidth of the amplifier 26.

The frequency bandwidth control unit 27 controls the auxiliary scan feeding pitch (translation speed) of the inspection object moving stage 102 according to the distance from the rotation center to the illumination spot 3 (radius r) in the main scan of the semiconductor wafer 100. As mentioned above, when the scattered or diffracted or reflected light) from the foreign object 1 is detected by the optical detector 7, the scattered light signal is generated continuously throughout the time period during which the foreign object 1 crosses the minor diameter d2 of the illumination spot 3. Under the constant angular speed condition, the linear speed is proportional to the radius r of the position of the illumination spot 3, and the time period is inversely proportional to the radius r when the minor diameter d2 is not changed. Thus, the frequency bandwidth Δf necessary for letting through the time-varying waveform of the scattered light signal from the optical detector 7 is proportional to the radius r. Therefore, the frequency bandwidth control unit 27 controls the frequency bandwidth Δf (in the amplification of the output signal (scattered light signal of the optical detector 7) proportionally to the radius r of the position of the illumination spot 3.

The digital data from the A/D converter 30 is compared with a preset detection threshold value by the foreign substance/defect judgment mechanism 108. If the digital data is the threshold value or higher, the foreign substance/defect judgment mechanism 108 judges that the digital data derives from a foreign substance/defect, monitors subsequent variations in the value of the digital data, and generates the foreign substance/defect judgment information upon detecting a maximum value. In response to the generation of the foreign substance/defect judgment information, the foreign substance/defect coordinate detecting mechanism 130 calculates the coordinate position of the detected foreign substance/defect. Subsequently, the particle size calculating mechanism 120 calculates the size of the detected foreign substance/defect from the maximum value of the digital data. In this case, the magnitude of the digital data caused by the foreign substance/defect changes proportionally to the illuminance of the illumination spot 3 even when the size of the foreign substance/defect is constant. Therefore, the digital data to be used for the calculation of the size of the detected foreign substance/defect is previously corrected based on the change in the illuminance of the illumination spot 3 caused by the change in its area.

Figure 5:
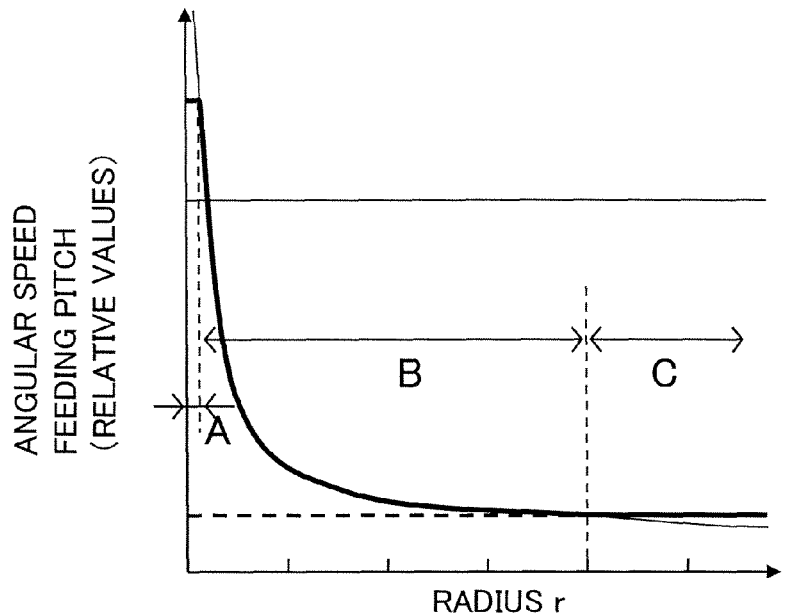
FIG. 5 is a graph showing an example of the relationship among the position, the angular speed and the feeding pitch of the illumination spot on the surface of the inspection object in the second embodiment of the present invention.

In FIG. 5, the vertical axis represents the speed (angular speed) of the rotation of the semiconductor wafer 100 in the main scan direction by the rotating stage 103 of the inspection object moving stage 102 and the speed of the translation of the semiconductor wafer 100 in the auxiliary scan direction by the translating stage 104 (i.e., moving distance of the translating stage 104 in one rotation of the rotating stage (feeding pitch)). The horizontal axis represents the distance r from the center of the wafer 100 to the illumination spot 3 (radius r). The semiconductor wafer 100 is segmented into three areas A, B and C based on the radius r from the rotation center. The area A is the closest to the rotation center. The area C is the farthest from the rotation center (peripheral part of the semiconductor wafer 100). The area B is the intermediate area between the areas A and B.

The angular speed is constant (b1) irrespective of the radius r.

The feeding pitch is constant (a1) in the area A, decreases substantially inversely proportionally to the square root of the radius r in the area B, and is constant (c1) in the area C. Thus, the areas A, B and C will be referred to as an "inner constant feeding pitch area", a "feeding pitch control area" and an "outer constant feeding pitch area", respectively.

Next, the surface inspection time T (1), the detection sensitivity (2) and the thermal damage (3) will be examined by use of an example of numerical values.

(1) Surface Inspection Time T

First, a semiconductor wafer 100 with a diameter of 300 mm will be considered as an example. The inspection time it takes for inspecting (scanning) the whole area of the semiconductor wafer 100 is assumed to be T. The major diameter d1 of the illumination spot 3 and the feeding pitch pi in the i-th main scan rotation in each area (inner constant feeding pitch area (area A in FIG. 5), feeding pitch control area (area B in FIG. 5), outer constant feeding pitch area (area C in FIG. 5)) are defined as follows:

inner constant feeding pitch area: 0 mm$\leq$r$\leq$1.5625 mm, d1=0.4 mm, pi=0.2 mm
    feeding pitch control area: 1.5625 mm$\leq$r$\leq$100 mm, d1=0.5/$r^{1/2}$ mm, pi=0.25/$r^{1/2}$ mm
    outer constant feeding pitch area: 100 mm$\leq$r$\leq$150 mm, d1=0.05 mm, pi=0.025 mm The numbers of main scan rotations in each area defined as above are as follows:

inner constant feeding pitch area: $1 \leq i \leq 7$
    feeding pitch control area: $8 \leq i \leq 2668$
    outer constant feeding pitch area: $2669 \leq i \leq 4668$ The total number M of main scan rotations is 4668 (M=4668).

If we assume here that d1=0.05 mm (constant) and pi=0.025 mm (constant) in all of the areas A, B and C, the total number M of main scan rotations amounts to 150/0.025=6000.

As above, in the case where the main scan rotation is executed at a constant angular speed, the surface inspection according to this embodiment is capable of reducing the inspection time to approximately (1/1.3)T in comparison with the inspection time T necessary when the inspection (scanning) is conducted by setting d1 and pi constant in all the areas of the semiconductor wafer 100.

(2) Detection Sensitivity

Next, the detection sensitivity to the foreign object will be examined.

The net signal quantity S of the scattered light signal obtained when the scattered light from the foreign object 1 is detected by the optical detector 7 is proportional to the <illuminance of the illumination spot>, while the noise level N is proportional to the square root of <illuminance of the illumination spot>×<area of the illumination spot>×Δf. Consequently, the S/N ratio as the ratio between the net signal quantity S and the noise N is proportional to the square root of {<illuminance of the illumination spot>/(<area of the illumination spot>×Δf)}. If we assume that the intensity of the whole illuminating light 21 and the minor diameter d2 of the illumination spot 3 are kept substantially constant during the inspection, when the major diameter d1 of the illumination spot 3 is controlled inversely proportionally to the square root of radius r of the position of the illumination spot 3, the S/N ratio is maintained substantially constant in regard to the above factors since the <illuminance of the illumination spot> is proportional to the square root of the radius r, the <area of the illumination spot> is inversely proportional to the square root of the radius r and the frequency bandwidth Δf is proportional to the radius r. Therefore, while the rotating stage 103 is driven at a constant angular speed, the translating stage 104 is driven as shown in FIG. 5. In the feeding pitch control area (area B in FIG. 5) other than the inner constant feeding pitch area (area A in FIG. 5) in the central part of the semiconductor wafer 100 or the outer constant feeding pitch area (area C in FIG. 5) in the peripheral part, the translating stage 104 is driven so that the feeding pitch p (moving distance of the translating stage 104 in one rotation of the rotating stage 103) is substantially inversely proportional to the square root of the distance between the main scan rotation center and the illumination spot 3, that is, the square root of the radius r of the position of the illumination spot 3. In the inner constant feeding pitch area (area A in FIG. 5) and in the outer constant feeding pitch area (area C in FIG. 5), the translating stage 104 is driven at a constant feeding pitch p. Meanwhile, the major diameter d1 is also controlled in sync with the change in the feeding pitch p, to be substantially inversely proportional to the square root of the radius r of the position of the illumination spot 3. With the above control, the detection sensitivity in the feeding pitch control area (area B in FIG. 5) becomes substantially constant in this area as explained above. Since the detection sensitivity in the inner constant feeding pitch area (area A in FIG. 5) and the outer constant feeding pitch area (area C in FIG. 5) is similar to that in the first embodiment, it can be concluded in this embodiment that detection sensitivity equivalent to that in the conventional technique is achieved in the outer constant feeding pitch area (area C in FIG. 5) and at least detection sensitivity equivalent to or higher than that in the outer area can be secured in the areas inside the outer area.

(3) Thermal Damage

Next, the thermal damage to the semiconductor wafer 100 in the inspection will be examined. Since the intensity of the whole illuminating light 21 used for the illumination is kept substantially constant and the area of the illumination spot 3 increases with the decrease in the radius r in this embodiment as mentioned above, the illuminance of the illumination spot 3 decreases with the decrease in the radius r. Therefore, this embodiment is also capable of suppressing the increase in the thermal damage to the surface of the semiconductor wafer 100 in the inspection (which is light in the peripheral/outer part of the semiconductor wafer 100) with the decrease in the radius r.

The other configuration is similar to that in the first embodiment.

Also in this embodiment configured as above, the auxiliary scan feeding pitch (translation speed) on the semiconductor wafer 100 is controlled according to the distance from the rotation center to the illumination spot 3 in the main scan of the semiconductor wafer 100. Therefore, the inspection time can be shortened while the deterioration in the detection sensitivity and the increase in the thermal damage during the surface inspection are suppressed similarly to the first embodiment.

Third Embodiment

A third embodiment in accordance with the present invention will be described below referring to FIGS. 6 and 7.

Figure 6:
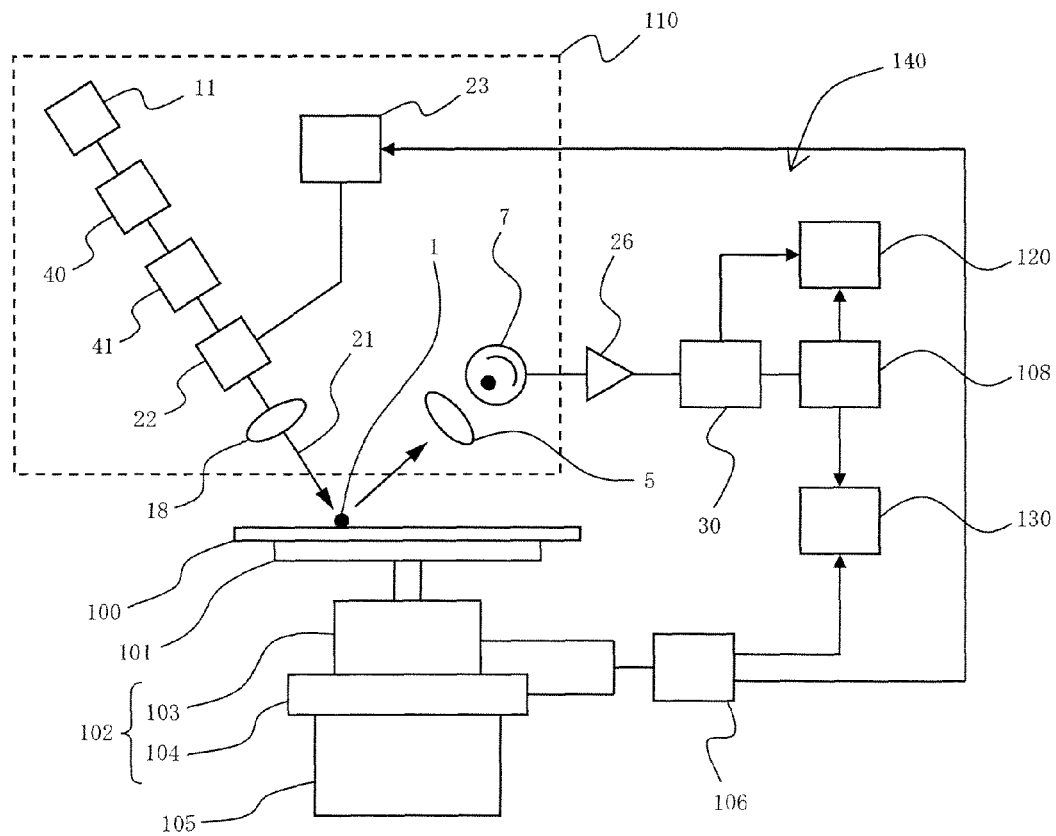
FIG. 6 is a schematic block diagram showing the overall configuration of a surface inspecting apparatus in accordance with a third embodiment of the present invention.

FIG. 6 is a schematic block diagram showing the overall configuration of a surface inspecting apparatus in accordance with the third embodiment of the present invention, wherein elements equivalent to those shown in FIG. 1 are assigned the same reference characters as those in the figure and repeated explanation thereof is omitted for brevity. The surface inspecting apparatus in this embodiment includes a beam splitting mechanism 22 and a beam interval control mechanism 23 instead of the beam width shaping optical system 14 and the beam width control mechanism 16 in the first embodiment. Multiple illumination spots 3 are formed on the semiconductor wafer 100 and the overlap ratio of the illumination spots 3 is controlled so that the overlap ratio increases with the increase in the distance from the main scan rotation center of the semiconductor wafer 100 to the illumination spot 3.

Figure 7:
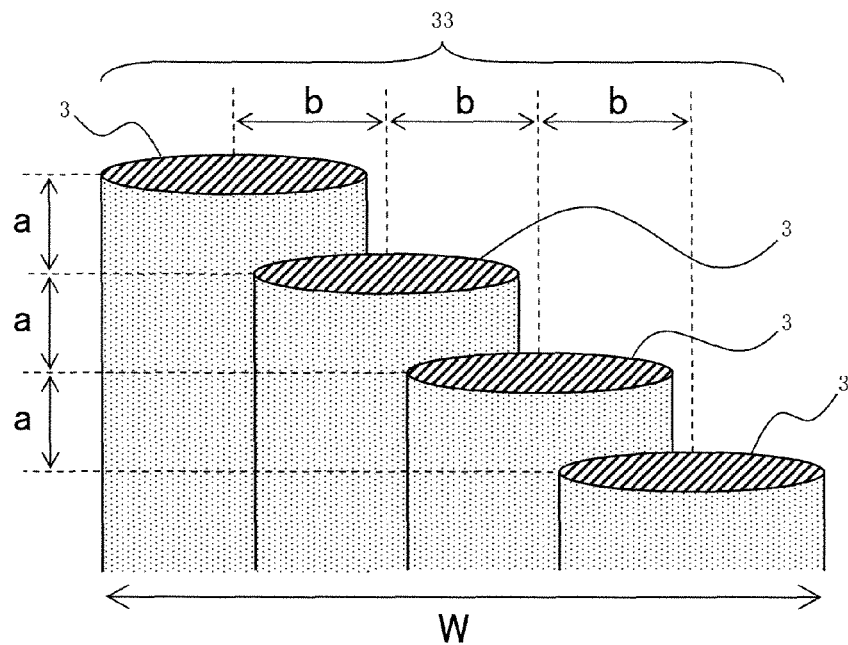
FIG. 7 is a schematic diagram showing illumination spots on the surface of the inspection object in the third embodiment of the present invention.

In FIG. 6, the beam splitting mechanism 22 splits the laser light (beam) into multiple (e.g. four) beams of illuminating light 21 illuminating the surface of the semiconductor wafer 100, by which multiple (e.g. four) illumination spots 3 are formed (see FIG. 7).

FIG. 7 is a schematic diagram showing an illumination spot set 33 on the surface of the inspection object in the third embodiment of the present invention.

In FIG. 7, the vertical direction is in parallel with the main scan direction of the inspection object moving stage 102, and the horizontal direction is in parallel with the auxiliary scan direction (orthogonal to the main scan direction).

The illumination spots 3 are formed with respect to a center in the main scan direction and the auxiliary scan direction, at regular intervals "a" in the main scan direction and "b" in the auxiliary scan direction. The interval b is set so that tracks drawn by the four illumination spots 3 according to the main scan will overlap. The width W of the track of the illumination spots 3 in the auxiliary scan direction is an effective illumination width of the illumination spot set 33. While the interval a is kept substantially constant during the surface inspection, the interval b is controlled by the beam interval control mechanism 23 substantially inversely proportionally to the radius r of the center position of the illumination spot set 33. With this control, the effective illumination width W can be changed substantially inversely proportionally to the radius r.

The other configuration is similar to that in the first embodiment.

Also in this embodiment configured as above, the inspection time can be shortened while the deterioration in the detection sensitivity and the increase in the thermal damage during the surface inspection are suppressed similarly to the first embodiment.

Incidentally, it goes without saying that the beam interval control mechanism 23 in this embodiment may also be configured so as to control the interval b substantially inversely proportionally to the square root of the radius r of the center position of the illumination spot set 33 and such a beam interval control mechanism 23 may be employed in place of the means for changing the effective illumination width W in the second embodiment.

Fourth Embodiment

A fourth embodiment in accordance with the present invention will be described below referring to FIG. 8.

Figure 8:
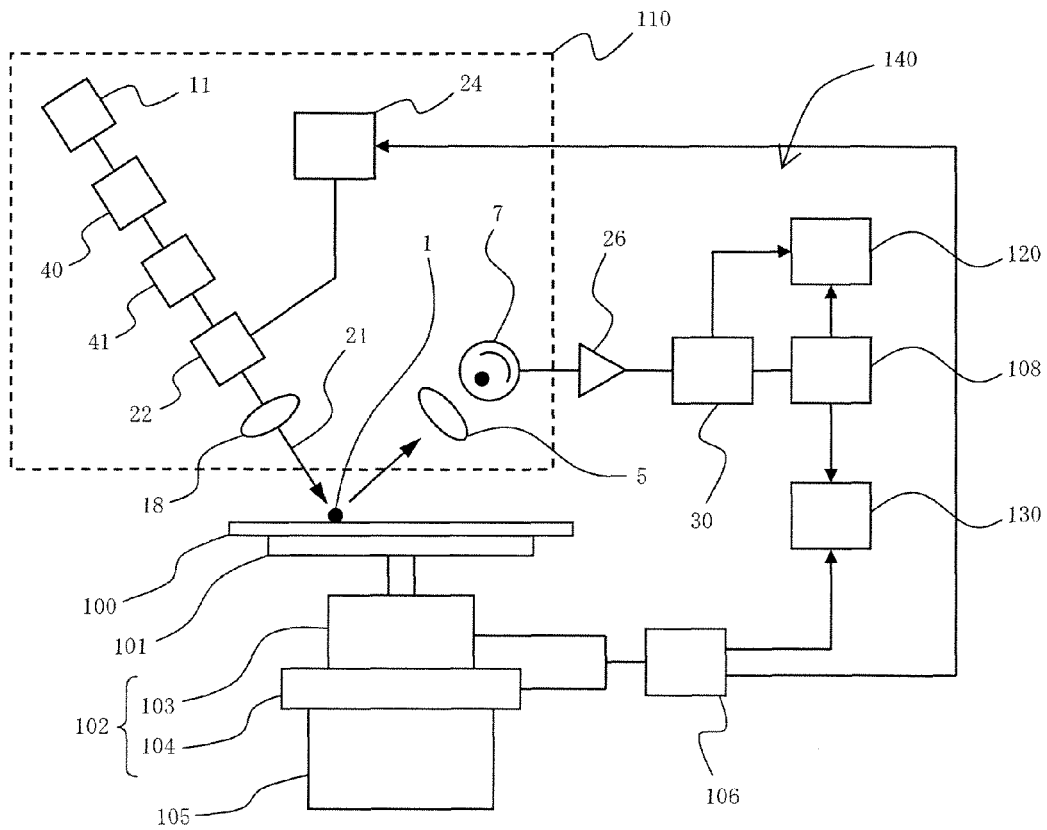
FIG. 8 is a schematic block diagram showing the overall configuration of a surface inspecting apparatus in accordance with a fourth embodiment of the present invention.

FIG. 8 is a schematic block diagram showing the overall configuration of a surface inspecting apparatus in accordance with the fourth embodiment of the present invention, wherein elements equivalent to those shown in FIG. 1 or 6 are assigned the same reference characters as those in the figure and repeated explanation thereof is omitted for brevity. The surface inspecting apparatus in this embodiment includes a beam number control mechanism 24 instead of the beam interval control mechanism 23 in the third embodiment. Multiple illumination spots 3 are formed on the semiconductor wafer 100 and the number of the illumination spots 3 is controlled so that the number decreases with the increase in the distance from the main scan rotation center of the semiconductor wafer 100 to the illumination spot 3.

In FIG. 8, the beam splitting mechanism 22 splits the laser light (beam) into multiple (e.g. four) beams of illuminating light 21 illuminating the surface of the semiconductor wafer 100, by which multiple (e.g. four) illumination spots 3 are formed (see FIG. 7).

In this embodiment, the intervals a and b are kept substantially constant during the surface inspection, while the number of the illumination spots 3 forming the illumination spot set 33 is controlled by the beam number control mechanism 24 substantially inversely proportionally to the radius r of the center position of the illumination spot set 33. With this control, the effective illumination width W can be changed substantially inversely proportionally to the radius r.

The other configuration is similar to that in the third embodiment.

Also in this embodiment configured as above, the inspection time can be shortened while the deterioration in the detection sensitivity and the increase in the thermal damage during the surface inspection are suppressed similarly to the first and third embodiments.

Incidentally, it goes without saying that the beam number control mechanism 24 in this embodiment may also be configured so as to control the number of the illumination spots 3 substantially inversely proportionally to the square root of the radius r of the center position of the illumination spot set 33 and such a beam number control mechanism 24 may be employed in place of the means for changing the effective illumination width W in the second embodiment.

DESCRIPTION OF REFERENCE CHARACTERS 1 foreign object
5 condensing lens 7 optical detector
11 light source
14 beam width shaping optical system
16 beam width control mechanism
18 illuminating lens
21 illuminating light
26 amplifier
30 A/D converter
40 light amount adjustment mechanism
41 beam expander
100 semiconductor wafer
101 chuck
102 inspection object moving stage
103 rotating stage
104 translating stage
105 Z stage
106 inspection coordinate detecting mechanism
108 foreign substance/defect judgment mechanism
110 illumination/detection optical system
120 particle size calculating mechanism
130 foreign substance/defect coordinate detecting mechanism
140 illumination/detection control system

The invention claimed is:

1. A surface inspecting method employing a surface inspecting apparatus, the surface inspecting apparatus comprising:
    an inspection object moving means for rotating the inspection object as a main scan and translating the inspection object as an auxiliary scan,
    illuminating means for illuminating a surface of the inspection object with illuminating light and thereby forming an illumination spot as an illumination area of the illuminating light,
    optical detector means for detecting scattered or diffracted or reflected light from the illumination spot, and
    foreign object detecting means for detecting a foreign object existing on the surface of the inspection object or in a part of the inspection object in the vicinity of the surface based on a result of the detection supplied from the optical detector means, wherein:
    translation speed of the auxiliary scan by the inspection object moving means is controlled according to distance from a rotation center of the inspection object in the main scan to the illumination spot, and
    rotation speed of the inspection object moving means in the main scan is kept constant.

2. The surface inspecting method according to claim 1, wherein the translation speed of the auxiliary scan by the inspection object moving means is controlled so as to decrease/increase the translation speed with the increase/decrease in the distance from the rotation center of the inspection object in the main scan to the illumination spot.

3. The surface inspecting method according to claim 1, wherein a diameter of the illumination spot in a direction orthogonal to the direction of the main scan is controlled so as to decrease/increase the diameter with the increase/decrease in the distance from the rotation center of the inspection object in the main scan to the illumination spot.

4. The surface inspecting method according to claim 1, wherein the translation speed of the auxiliary scan by the inspection object moving means is controlled substantially inversely proportionally to the distance from the rotation center of the inspection object in the main scan to the illumination spot.

5. The surface inspecting method according to claim 1, wherein a diameter of the illumination spot in a direction orthogonal to the direction of the main scan is controlled substantially inversely proportionally to the distance from the rotation center of the inspection object in the main scan to the illumination spot.

6. The surface inspecting method according to claim 1, wherein the translation speed of the auxiliary scan by the inspection object moving means is controlled substantially inversely proportionally to the square root of the distance from the rotation center of the inspection object in the main scan to the illumination spot.

7. The surface inspecting method according to claim 1, wherein a diameter of the illumination spot in a direction orthogonal to the direction of the main scan is controlled substantially inversely proportionally to the square root of the distance from the rotation center of the inspection object in the main scan to the illumination spot.

8. The surface inspecting method according to claim 1, wherein the illumination spot is in an elliptical shape.

9. The surface inspecting method according to claim 1, wherein:
    the illumination spot is made up of multiple illumination spots which are arranged so that at least part of tracks on the surface of the inspection object scanned by the illumination spots by the main scan of the inspection object overlap, and
    the number of the illumination spots is controlled so as to decrease/increase the number with the increase/decrease in the distance from the rotation center of the inspection object in the main scan to the illumination spot.

10. The surface inspecting method according to claim 1, wherein:
    the illumination spot is made up of multiple illumination spots which are arranged at different positions in regard to a direction orthogonal to a main scan direction of the inspection object so that at least part of tracks on the surface of the inspection object scanned by the illumination spots by the main scan overlap, and
    overlap ratio of the illumination spots is controlled so as to increase/decrease the overlap ratio with the increase/decrease in the distance from the rotation center of the inspection object in the main scan to the illumination spot.

* * * * *